(12) United States Patent
Gidekel et al.

(10) Patent No.: US 7,273,931 B2
(45) Date of Patent: Sep. 25, 2007

(54) PLANT PROMOTER

(76) Inventors: Manuel Gidekel, Carlos Dittborn 01045, Temuco, IX Region Chile (CL); Ana Gutierrez, Calros Dittborn 01055, Temuco, IX Region (CL); Leal Pamela, Rudecindo Ortega 02200 casa No: 3, Temuco, IX Region (CL); Luis Destefano-Beltran, 3644 36th Ave. SW. Apt. 116, Fargo, ND (US) 58104; Jorge Dinamarca, Saavendra 680, Victoria, Novena Region (CL); Emilio Guerra, Los Urales 01720, Temuco, IX Region (CL)

( * ) Notice: Subject to any disclaimer, the term of this patent is extended or adjusted under 35 U.S.C. 154(b) by 0 days.

(21) Appl. No.: 11/639,474

(22) Filed: Dec. 15, 2006

(65) Prior Publication Data

US 2007/0118922 A1    May 24, 2007

Related U.S. Application Data

(62) Division of application No. 11/120,351, filed on May 2, 2005, now abandoned.

(60) Provisional application No. 60/567,125, filed on May 2, 2004, provisional application No. 60/567,135, filed on Apr. 30, 2004.

(51) Int. Cl.
- *A01H 1/00* (2006.01)
- *C07H 21/04* (2006.01)
- *C12N 5/14* (2006.01)
- *C12N 15/09* (2006.01)

(52) U.S. Cl. .................. 536/24.1; 435/6; 435/91.4; 435/468; 435/419; 435/253.3; 435/320.1; 435/536; 536/23.1; 800/278; 800/295

(58) Field of Classification Search ............... None
See application file for complete search history.

(56) References Cited

OTHER PUBLICATIONS

Anderson et al. (NCBI, GenBank, Sequence Accession No. BQ162524, Published Apr. 24, 2002).*
Gidekel, Manuel et al. 2003: Identification and characterization of three novel cold acclimation-responsive . . . Extremophiles 7:459-469.
Deschampsia antarctica Dacor 1 coding sequence AY090541.

* cited by examiner

*Primary Examiner*—Phuong T Bui
*Assistant Examiner*—Vinod Kumar
(74) *Attorney, Agent, or Firm*—Dodds and Associates; Susanne Somersalo; John Dodds

(57) ABSTRACT

This disclosure provides gene sequence of a novel gene DaRub1 of *Deschampsia antarctica* expressed at low temperatures. The promoter sequence of this gene is identified and characterized. The promoter is inducible at low temperature, upon wounding and after auxin-treatment. Additionally this disclosure shows improved low temperature tolerance of transgenic Eucalyptus plants expressing DaRub1 gene.

13 Claims, 9 Drawing Sheets

```
CTGTTTGGCTTTATTTATAAAGCGGAACGAAAGCCTGTTTCGAAAAGAGAGAAGTCACGACGGACCAAACC
CATTTAGAGTAGCGACACTCGATGCCTCGCCATTTTCGTGAGGAATTTCCATAGTTGGCAAGTGATGTCAC
CTACTTCATGGTGCATTTAGAGTTGAGGCAGAGCTTACCCGGCATGTGTAAGGGTGGCAATATTCACTGTG
GGGACGAGTACCCGCGGGGAGTTACCCATCATGAAGCGGAGATGGGGGACAAATTCACCCCACGGGTATTG
TCTCATGGGCGGGGATGGGGAGCAAATCCTCCATGGATACCCGACGAACTATGCCATGTGAACTACAGAT
GCACAATATATAGATTAAAACCTAGATAGTCCACTTAATTTTTTTTCTCCATCTCTCTCAGCCACCTTGTC
CTTTCTAATCTCATTTATCACAGTCGACGCTGAGTTCCCATAGAGTCCCGACGGGTACCGGATACCCGTTA
TTGACAGGGATGGGGACAGTTTTGTCCCCGTGAAGGTTTATGGGGCTGGCGGGTATGAGGACTGGTGGGGT
TCGAGGTGAGGACGGCGGAGTCATCACCGGTCGTCTCAGTCCCCGTTGCCACCCTGAGGCGTGAGCAGAAC
TTAGGTCGCTCTTGCCAATATAGGTCAAACGGAAGCTAGAACTGATGCGTGGCTTCGTTCAGGGCCAGCAA
ACATACCTCAACTCTGTTTCGAGGATTGTAATCCGGTTGCTTTAAGTCCCATACCACCCCATTCGCGAAAA
GGAAAAACGAAAAGGATTTTGAGTAGACGAGTTTTTACATGCGACGCAAGCCGATGGGTGTCCAAACCAG
TTCGTCTGTACGTCCGTGGCATTTCGTGTGCACAACAGCACGAGTATAACATTTTATACGTACCTGAAGAT
TAGGATCAAGCGTCTTGCATAGTCTCAGGAGAAGGAAAAAAAAAAGGTCCCAACCGACGTTACAGAACGGG
TCGGAAGTCTGAGCCCGAGCGGAAAACCGGCTCACGGGGTTCCCCCGACTTGACGCCGCGCACCCTCAATA
AATCCACCGGGTCCCGAGGAAAAAGAAAGGAATTTTCGTTTGTTTCTGCCTCCGCTTCGTTCTCACGCAGA
CTTGACGCTCTCTCCTTGACCCCCCTCCCTCCACCCTCCAGGCCTCGCCGCCACACGGGAGCAGGAGGAGA
AGATGCAGATCTTCGTCAAGACCCTGACGGGGAAGACCATCACCCTCGAGGTGGAGAGCAGCGACACCATC
GATAACGTCAAGGCCAAAATCCAGGACAAAGAAGGGATTCCTCCAGACCAACAACGTTTGATATTTGCTGG
CAAGCAGTTGGAAGATGGACGCACACTTGCTGATTACAATATTCAAAAGGAGTCTACTCTTCACTTGGTCC
TCAGGCTCAGGGGCGGTACTATGATCAAGGTTAAGACACTCACTGGAAAGGAGATCGAAATTGACATTGAG
CCCACTGACACGATTGATAGGGTCAAGGAGCGTGTTGAGGAGAAAGAAGGCATTCCTCCCGTGCAGCAAAG
GTTGATTTATGCTGGTAAGCAGCTTGCAGATGACAAGACTGCGAAGGACTACAACATCGAAGGTGGCTCCG
TCCTCCATCTTGTACTTGCTCTGAGGGGTGGTTACTAGTAAATCTAGCTAGTGACACTACTTGCCTCAATC
TACTCTAATGGTTGAGAGAAGTGACTATTGGTGGTATGGAACTAGATAATAACAAGTAACAAACTAGCTTT
TCCTAGTGGGAGGGGCTGTCTTCCATGTTATTATCTTGTATGATTTGATAAAATCACTCCCTAGTTTATCT
GCCTCTGTTGTTATGTCTGCTGTGTGAGAAATCCATGATCATCTGAAAAAAAAAAAAAAAAAAAAAAA
AAA
```

PLANT PROMOTER

PRIORITY

This application is a divisional application of non provisional application No. 11/120,351 filed May 2, 2005 now abandoned and claims priority of the U.S. provisional applications No. 60/567,125 filed May 2, 2004 and 60/567,135 filed Apr. 30, 2004.

SEQUENCE DATA

This application contains sequence data provided on a computer readable diskette and as a paper version. The paper version of the sequence data is identical to the data provided on the diskette.

BACKGROUND OF THE INVENTION

1. Field of the Invention

The present invention relates to the field of improved stress tolerance of plants, more specifically to genes and promoter sequences expressing at low temperatures and even more specifically to low temperature tolerance improved by means of gene transfer.

2. Background

Low temperature is one of the major limiting factors of growth, development and geographical distribution of plants. Some plants are able to acclimate by increasing their freezing tolerance upon exposure to low non-freezing temperature. This process involves physiological and biochemical changes, many of which are regulated through qualitative and quantitative modification of gene expression leading to the accumulation of newly synthesized proteins and mRNAs.

A number of genes having expression induced by low temperature have been isolated and characterized in a wide range of species. Most of the studies of gene expression during cold acclimation have been performed in plants from temperate and semi-temperate climates. Differently to this approach, our approach has been to study gene expression of genes induced by cold acclimation in a highly freezing tolerant plant. *Deschampsia antarctica* Desv. (Poacea) is a highly tolerant plant to the harsh freezing conditions and it is one of the two vascular plant species that have naturally colonized Maritime Antarctic Peninsula. A high accumulation of soluble carbohydrates, especially sucrose and fructans has been found in leaves of *D. antarctica* during growth period in the Antarctic summer. Total protein extracts from leaves of *D. antaratica* growing in the Antarctica has been shown to have a high cryoprotective activity on barley chloroplasts. Membrane lipid contents and the degree of unsaturation of fatty acids in the leaves do not differ significantly from plants in temperate zones. The optimal photosynthetic activity of this species is at 13° C. and it can maintain up to 30% of this rate at 0° C. Cold acclimation experiments have shown that *D. antarctica* is able to acclimate from −14.8° C.($LT_{50}$ at −14° C.) to −26.8° C. when growing at +2/−1.5° C. for 21 days in a solid substrate in the laboratory.

Due to the high capacity of cold acclimation that this species possesses we were interested of its gene expression during the acclimation. Not only is there a need to characterize genes that are responsible for low temperature tolerance of plants but there is also a need for characterization and identification of new plant promoters. Characterization and identification of such genes and their promoters will be greatly useful in the improvement of various crops. There is a clear need to improve low temperature tolerance of various sensitive plant species. Furthermore, in plant breeding and research there is a constant need for plant promoters inducible by various environmental factors such as low temperature.

Therefore, one object of the present disclosure is to increase cold resistance or tolerance of plants through gene transfer, especially of fruit trees such as, but not limited to eucalyptus, avocado, orange and peach trees. The system can be applied both to monocots and to dicots.

Another object of this invention is to reduce photo inhibition caused by chilling temperatures.

Still another object of the present invention is to provide transgenic plants, plant cells, plant tissue, plant organs or plant components of plants such as, but not limited to *Arabidobis thaliana* or *Eucalyptus globulus* carrying a recombinant transgene capable of expressing a modified transcript of a related-to-ubiquitin protein of *Deschampsia antarctica*.

An even further object of the present invention is to provide promoters inducible by low temperatures, wounding and auxin treatment. *Eucalyptus globulus* has become one of the most important forest species, for example, in Chile due to its fast growth and good wood quality especially for the purposes of pulp manufacturing. Currently, it represents the second most planted species in Chile, amounting approximately, along with other eucalyptus species, to a total of 350,000 hectares. However, strong world market competition makes it necessary to develop better technologies for its cultivation. Despite of its excellent characteristic there are wide surface areas of up to 2 million hectares where growth limiting restrictions are found. In particular areas, such as foothills of Andean Mountains and Chile's Center Valley, the poor cold tolerance of *Eucalyptus* species has been a limiting factor to expand cultivation.

The present disclosure resolves the problem of low freezing tolerance of trees such as eucalyptus by a method rendering transgenic plants able to tolerate lower temperatures. In addition to eucalyptus this method is applicable to various low temperature susceptible plants such as peach.

BRIEF DESCRIPTION OF THE DRAWINGS

FIG. 1. Depicts the nucleotide sequence of the full length of the gene DaRub1 (SEQ ID NO: 1). The first 1089 nucleotides represent the promoter sequence (SEQ ID NO: 2). The transcript initiation site is shown bold and underlined. The coding sequence (SEQ ID NO: 3) is shown with bold letters.

(A) Total RNA of Arabidopsis plants: wild type (wt), transgenic lines L1, L2, L3 and ΔAUBQ-RUB (empty vector) was extracted and hybridized with a UBQ-RUB probe (top panel). Sample loading (20 20 μg) was monitored using a 28S RNA probe (central panel). siRNA (50 μg) was hybridized with an anti-sense transcript corresponding to the UbiRub 3'-UTR (bottom panel)

Figure 4:
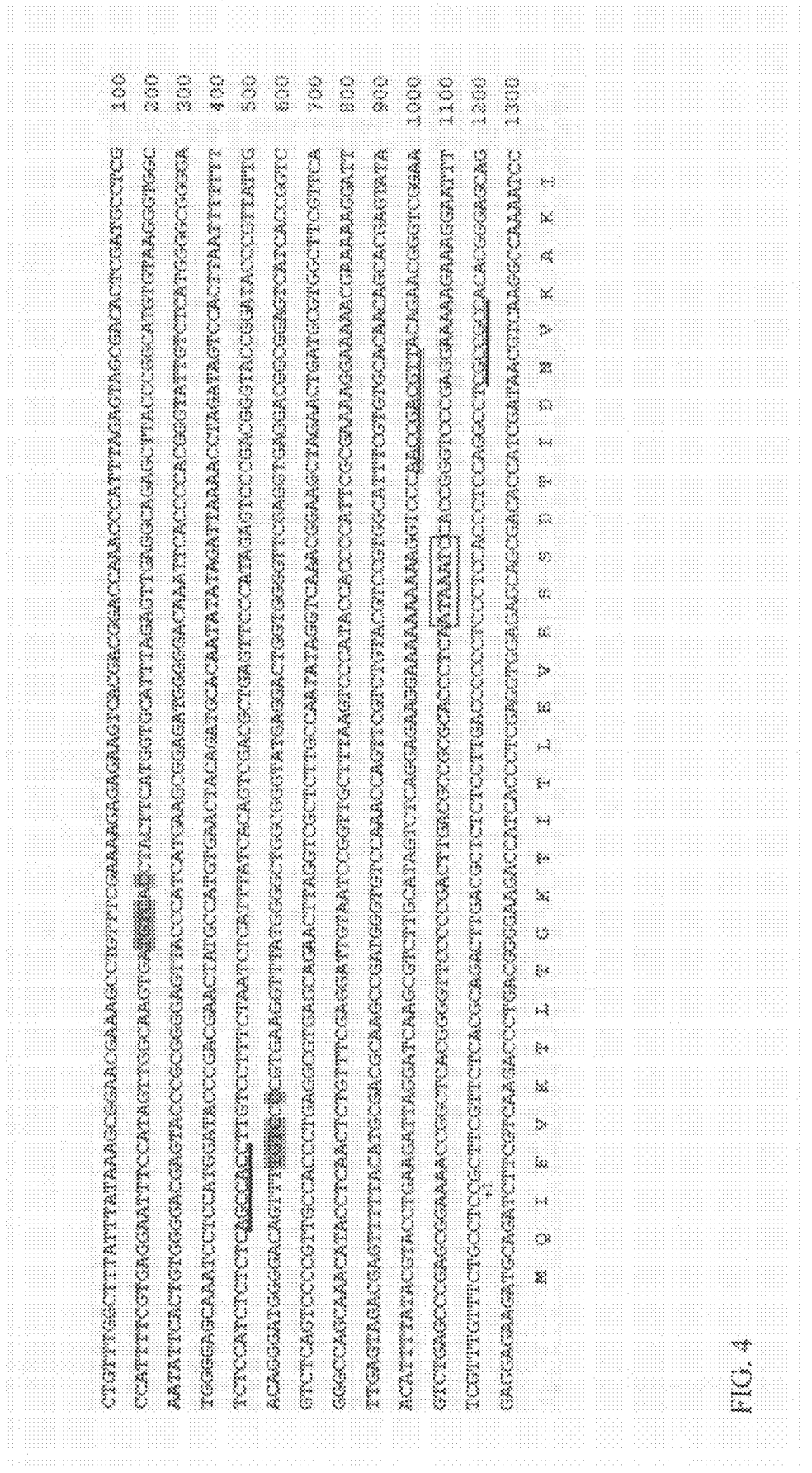

(B) Total protein (15 μg) of *A. thaliana* wild-type, transgenic lines L1, L2, L3 and ΔUBQ-RUB (vector alone) plants were separated by SDS-PAGE, blotted on nitrocellulose membranes, and probed with a UBQ-RUB polyclonal antibody FIG. 4: DaRub1 gene putative promoter sequence (SEQ ID NO: 2) and 5'-terminal cDNA sequence. Putative responding elements and TATA box are indicated: Auxin Responding Elements (AuxRE) (grey nucleotides), Ethylene Responding Elements (ERE) (underlined nucleotides), Dehydration Responding Element (DRE) (double underlined nucleotides), TATA box (boxed nucleotides). +1 indicate Transcription Initiation Site.

Figure 5:
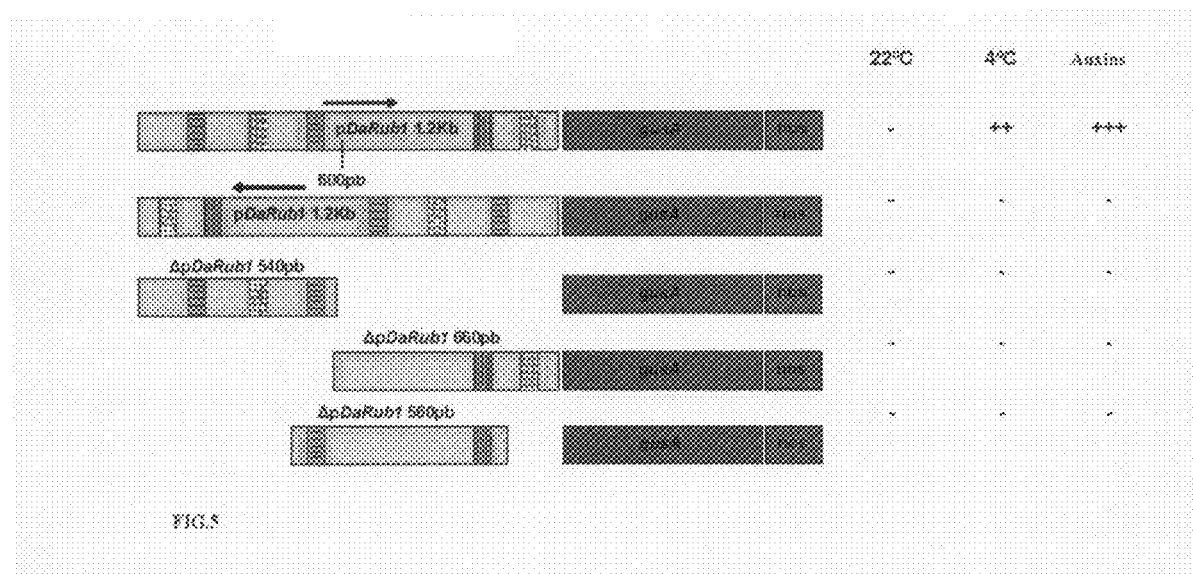

FIG. 5. Schematic representation of the DaRub1 promoter region and its deletion. The constructions were named according pb length fragment. Blocks with horizontal lines depict ERAux blocks, gray blocks with white dots depict ERR -blocks, blocks with vertical lines depict ERD-blocks. Arrows indicates the cloning direction of complete promoter region (sense and antisense). To the right a summary of the transgenic *Arabidopsis* plant response of each one of the reporter fusions, during control temperature (22° C.), cold acclimation temperature (4° C.) and auxin treatment: (−) indicates no response; (+++) indicates a strong response and (++) indicates a relatively strong response.

Figure 6:
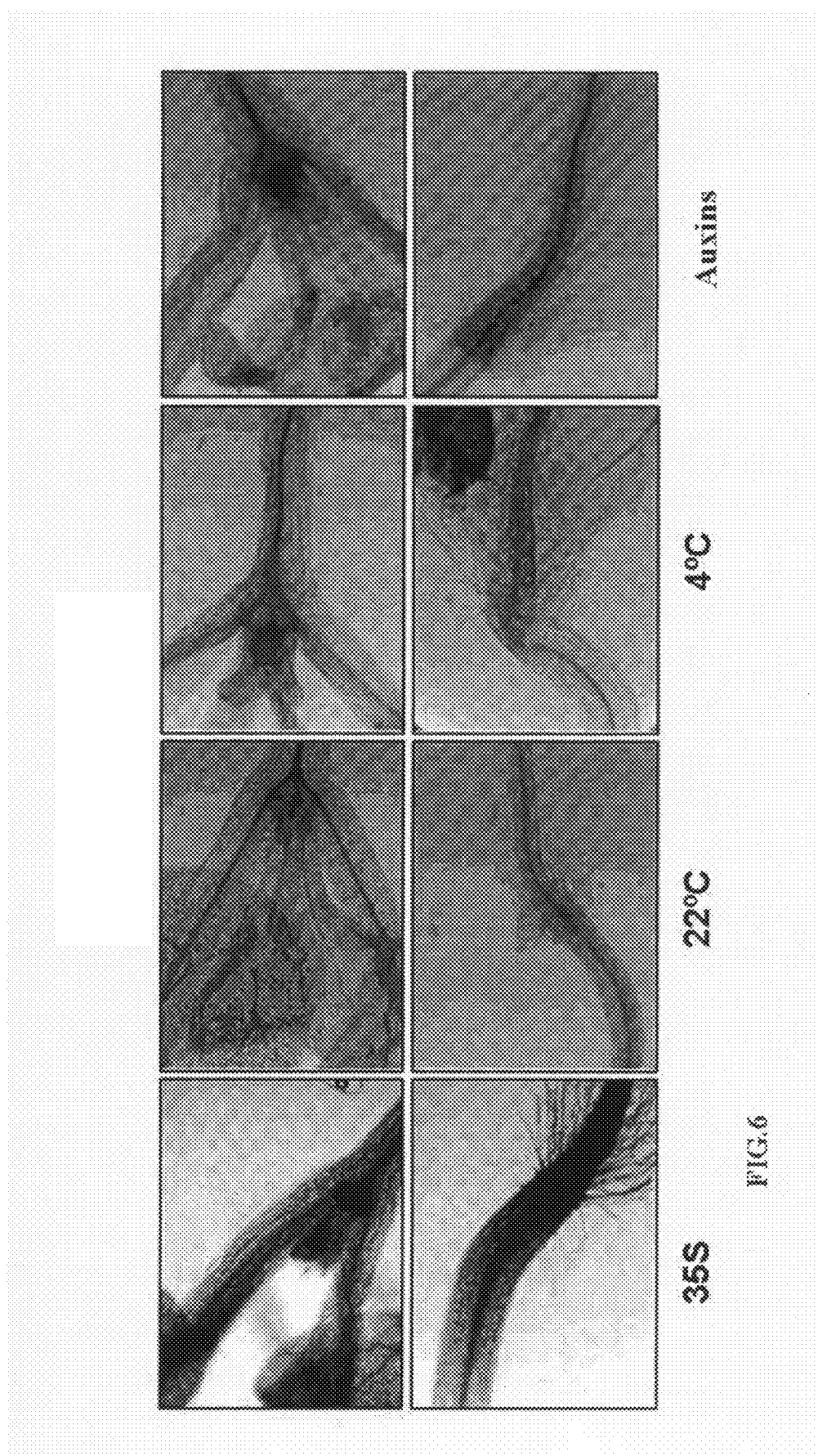

FIG. 6. GUS expression in fusion pDaRub1/gusA *A. thaliana* transgenic lines, during cold acclimation and auxin treatment. Cold acclimated (4° C.) and auxin-treated plantlets were kept in X-Gluc substrate and GUS expression was observed. 35S: positive control plants (pCAMBIA 1303), 22° C.: plants maintained at 22° C., negative control; 4° C.: one hour cold acclimated plants; Auxin: 1.0 μM of 2,4D treated plants. All the photographs represent 40× magnification.

Figure 7:
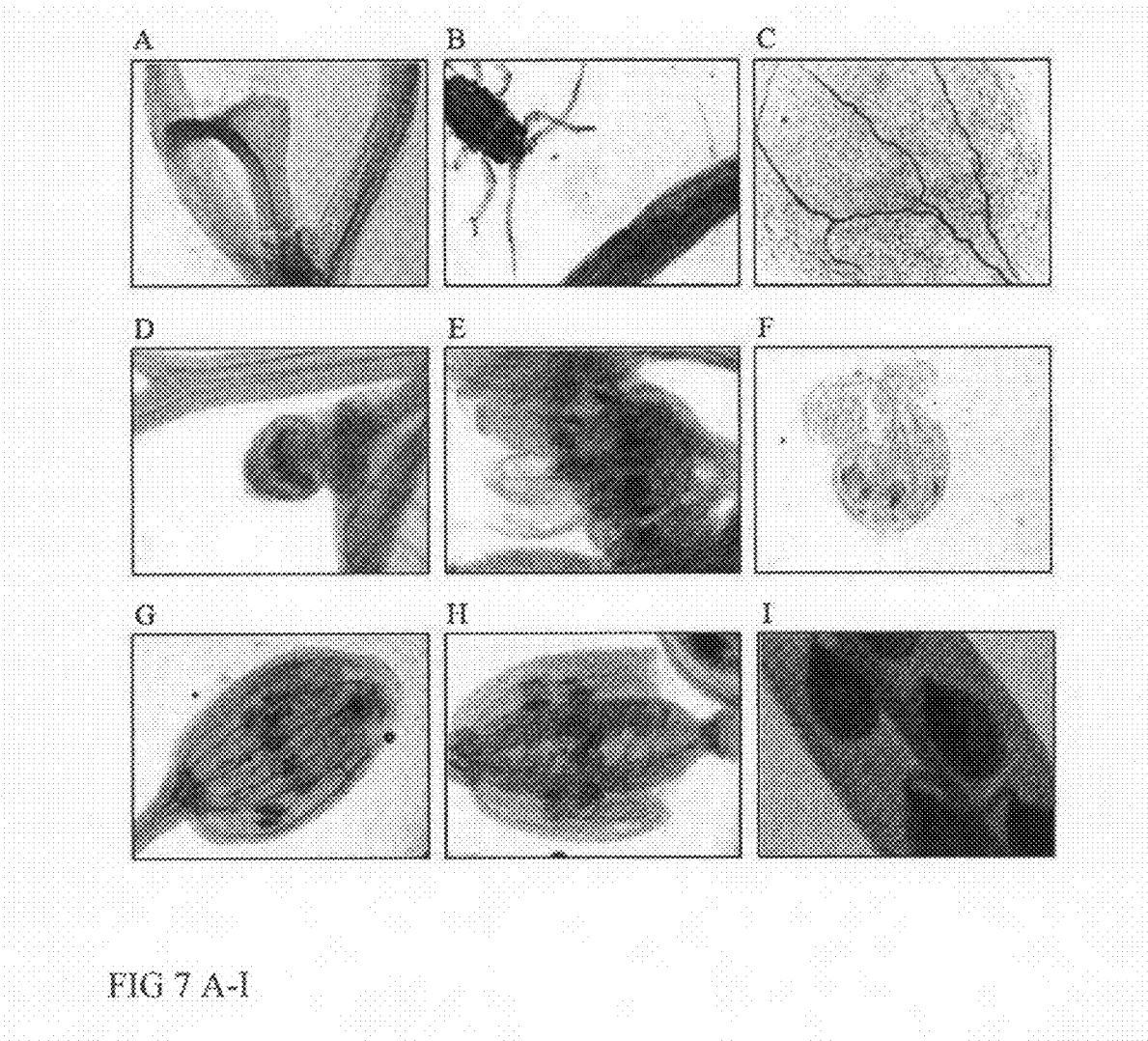

FIG. 7. GUS expression in fusion DaRub1/gusA *A. thaliana* transgenic lines, during wound and in different flower development phases. A and B: injuries by wounds, A: mechanical damage, B: damage by aphid infection; C: senescent leaves; D-H: different flower developments phases, F: 100× approach of D; I: silique. All the photographs represent 40× magnification, except F, that represents 100× magnification.

Figure 8:
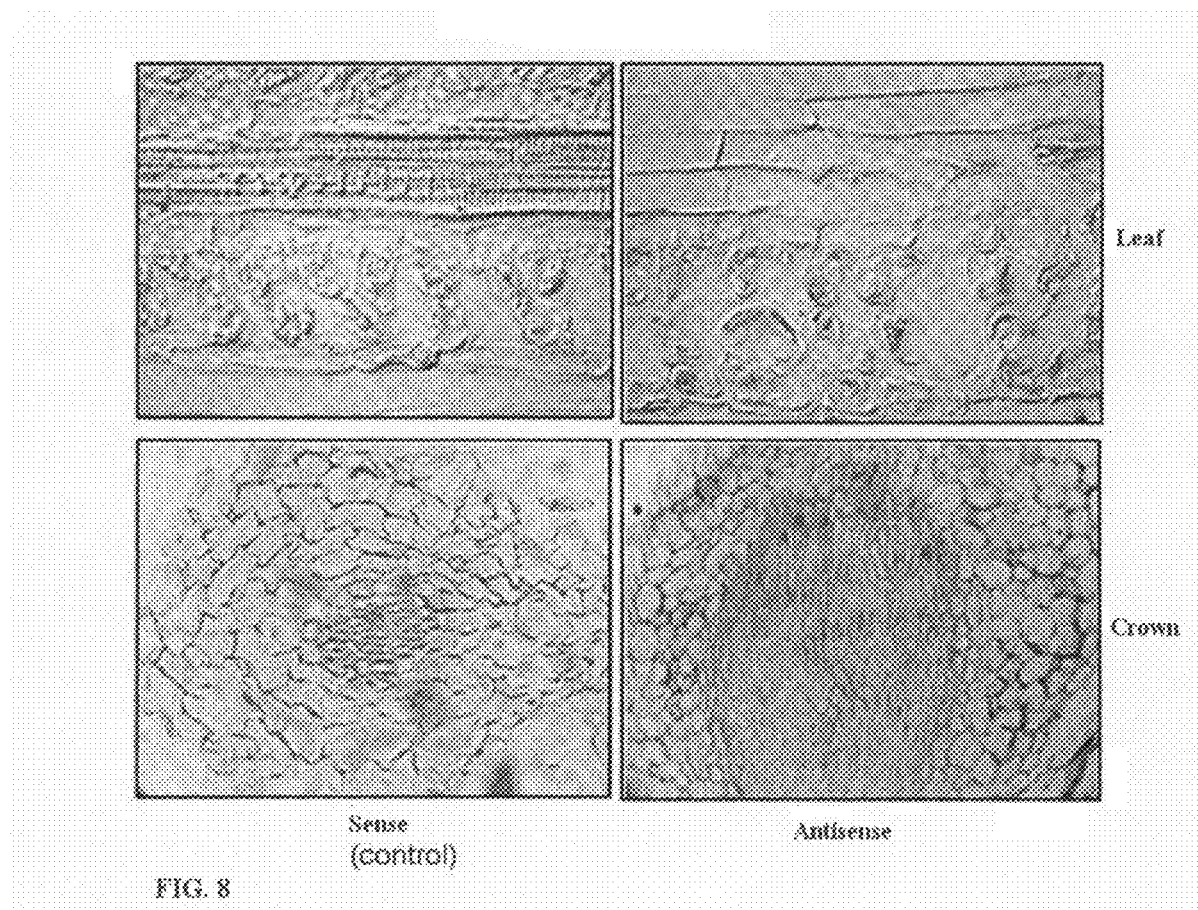

FIG. 8. DaRub1 antisense RNA in situ hybridization in *D. antarctica*. RNA obtained from DaRub13' UTR cDNA sequence was utilized for the tissue in situ hybridization (leaves and crown) of *D. antarctica* plants cold acclimated for 24 hours. A sense RNA probe was utilized like control.

Figure 9:
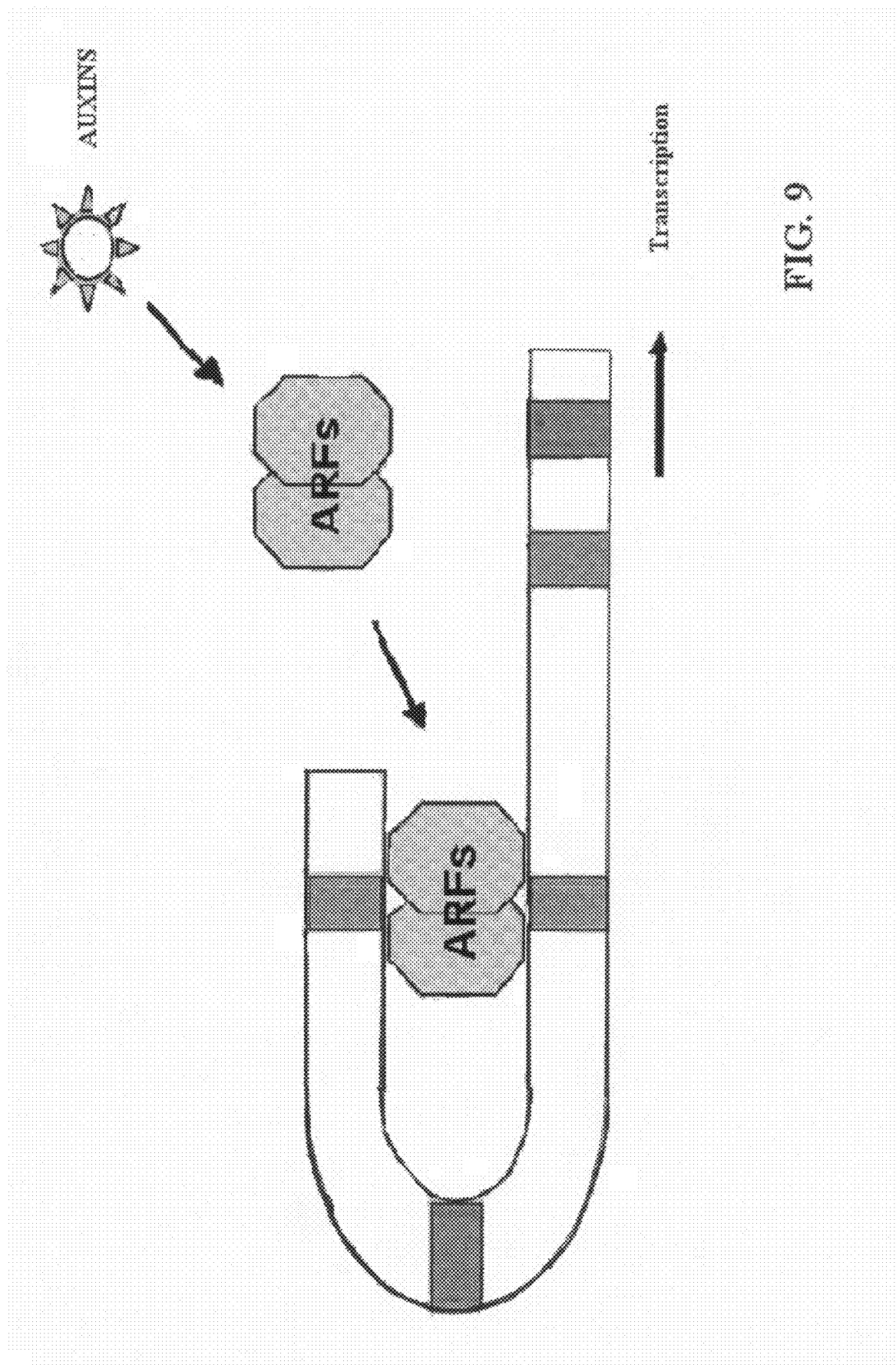

FIG. 9: Proposed model for transcription induction by AuxER of DaRub1 promoter region. ARFs: Auxin response factors.

DETAILED DESCRIPTION OF THE INVENTION

During the exposure of plants to low temperature many physiological and biochemical changes occur which lead to the development of freezing tolerance. The survival of tolerant plants at freezing temperatures depends on the timely modulation of different set of genes, the accumulation of both mRNAs and protein products of such genes correlates with the development of freezing tolerance. A major difficulty is the fact that many low temperature responsive genes are also induced by other stimuli, such as drought, abscisic acid (ABA) and salinity. It is unclear, however, how such different stimuli converge to induce the same gene. For example, it has been reported that low temperature and ABA regulate gene expression through separate transduction pathways. An alternative explanation is that several cis-acting elements are present in the promoter regions of these genes that respond to multiple factors.

Ubiquitin (UBQ) is one of the most conserved proteins among eukaryotes. The covalent attachment of UBQ to other proteins targets them for degradation by the 26S proteosome. Attachment of the ubiquitin carboxyl terminus to ε-amino lysyl-groups of substrate proteins requires ubiquitin-activating enzyme (E1), in an adenosine 5'triphosphate-(ATP)-dependent reaction in which a thiolester bond is formed between the COOH-terminus of UBQ and a cysteine within the E1 enzyme. The UBQ-moiety is transferred to a cysteine residue of ubiquitin-conjugating enzymes (E2). Finally, UBQ is covalently attached to a target protein by an isopeptide linkage directly from E2 or by UBQ-protein ligase (E3), such as the SCF (Skp1, Cdc53, F box protein, respectively). Recently, several families of ubiquitin-like proteins (RUB; related to Ubiquitin) have been described. These RUB-protein families include the mouse protein Nedd-8, *Arabidopsis thaliana* ubiquitin UBQ7, and the *Saccaromyces cerevisae* protein ScRublp. *Arabidopsis* ubiquitin-like proteins have 62% identity to ubiquitin, 83% identity to Nedd-8, and 57% identity to ScRublp. The RUB family includes the plant RUB1, RUB2, and RUB3 of *A. thaliana*, and RUB1 of *Brassica napus*; the mammalian RUB of mouse, rat and human; an open reading frame with significant RUB identity from *C. elegans*, and the fungal RUBs. The *Arabidopsis* proteins RUB1 and RUB2 differ by only one amino acid at position 60. BnRUB1 and AtRUB1 encode identical proteins with the exception of the COOH-terminal additional amino acid.

Several studies in different models have shown that RUB proteins are conjugated to target proteins through the sequential action of RUB-activating and RUB-conjugating enzymes in a similar way as ubiquitin conjugation. In *Arabidopsis*, RUB1 is activated by an E1-like heterodimer AXR1/ECR1 and transferred, by an RUB-E2 enzyme called RCE1, to the cullin protein of a SCF complex. The unique targets for RUB modification are members of a cullin protein family. These cullins are subunits of E2 ligase protein of the $SCF_S$ complex. In *Arabidopsis*, an E3 complex called $SCF^{TIR1}$ cullin is required for auxin response and it seems to target AUX/IAA proteins for degradation.

We have now isolated and characterized a gene expressed during cold acclimation in *Deschampsia antarctica*. The gene is called DaRub1, and it has an open reading frame (ORF) encoding for a 153 amino acids polypeptide consisting of an ubiquitin monomer fused in the same ORF to a RUB protein. Northern blot analysis confirmed that this gene is expressed during the first hours of cold acclimation and maintained with different expression levels up to 12 hours of acclimation. Furthermore, we isolated the promoter region of DaRub1 gene and identified and characterized the 5'-regulatory region of this gene.

The present invention is directed toward a novel gene of *Deschampsia antarctica* expressed during acclimation and a promoter region of the gene. The invention is also directed to transgenic plants containing a modified gene transcript of *Deschampsia antarctica*.

The present disclosure includes: a) characterization and identification of a novel gene of *Deschampsia antarctica* expressed during cold acclimation; b) characterization of its promoter region by fusing it to a reporter gene and transforming the chimeric construct into *Arabidopsis* plants c) introducing into plant cells a transgene including a DNA encoding a modified version of a related-to-ubiquitin protein from *Deschampsia antarctica* operably linked to a promoter functional in plant cells to yield transformed plant cells; and d) regenerating a transgenic plant from the transformed cell, wherein the transcript of the modified version of the related-to-ubiquitin protein (RUB) interacts with signal transduction machinery of the plant, thereby increasing the level of cold-resistance or—tolerance in the transgenic plant. As a result the ice-nucleation and freezing temperatures are significantly lower in the transgenic plant.

Furthermore, the invention features a method for reducing the photo inhibition caused by chilling temperatures. The method includes: a) introducing into plant cells a transgene including a DNA encoding a modified version of a related-to-ubiquitin protein from *Deschampsia antarctica* operably linked to a promoter functional in plant cells to yield transformed plant cells; and b) regenerating a transgenic plant from the transformed cell, wherein the transcript of the modified version of the related-to-ubiquitin protein interacts with the photosynthetic machinery of the plant, thereby increasing the photochemical or non-photochemical quenching capacity in the transgenic plant. As a result the transgenic plant is more tolerant or resistant to adverse effects caused by photo inhibition.

Even further the invention according to this disclosure features a model explaining auxin dependent modification of RUBs.

The following examples are meant to be descriptive and by no means limiting of the various embodiments of the present invention.

EXAMPLE 1

Plant Material and Growth Conditions for Obtaining Cold Acclimated *Deschampsia antarctica* Plants

*Deschampsia Antarctica* Desv. (*Poaceae*) plants were collected in the Coppermine Peninsula on Robert Island, Maritime Antarctica (62° 22'S; 59° 43'W) during the austral summer and transported in plastic bags to the laboratory. Plants were propagated vegetatively in plastic pots using a soil: peat mixture (3:1), fertilized with 0.12 g/l Phostrogen (Solaris, Buckinghamshire, UK) once every 2 weeks, and maintained at 13° C. in a growth chamber with a photon flux density of 180 µmol $m^{-2}$ $s^{-1}$ at the top of the canopy and photoperiod of 21 h /3 h of light/dark. The light source consisted of cool-white florescent tubes (F40CW IGE, Charlotte, N.C., USA). Relative humidity was around 60-70%. Plants growing under these conditions were considered as controls. For cold-acclimation studies plants were maintained 4° C. at the same light and photoperiod conditions than control plants for different times (0-21 days). De-acclimated plants were obtained by returning cold-acclimated plants to normal growth conditions for 24 hours.

EXAMPLE 2

Construction of Cold-Acclimation cDNA Library and Identification of Cold-acclimation-responsive cDNAs by mRNA Differential Display Total RNA isolated from 24- and 48 h cold-acclimated *D. antarctica* leaves were pooled and used for cDNA library construction by means of the SMART cDNA Library Construction Kit (Clontech, Palo Alto, Calif., USA) and Gigapack II Gold Packaging Extract (Stratagene, La Jolla, Calif., USA), following the manufacturer's instructions. The primary library contained an estimated $5 \times 10^6$ independent clones with an average insert size of 1,200 bp. The library was amplified and stored in 7% DMSO at −80° C. The cDNA library was screened by in situ plaque hybridization with a random-primed $^{32}$P-labeled probe of differential display clone D0-B 1.

*D. antarctica* cold-acclimation gene expression was studied by mRNA differential display using leaf total RNA extracted from non-acclimated and cold -acclimated *Deschampsia antarctica* plants taken at different intervals of treatment. A total of 38 cDNA bands were found to exhibit differential expression. Fragments were cut out of the gels, reamplified by PCR, and sub cloned into the pGEM-Easy vector. Twenty three partial cDNAs were shown by Northern blot analysis to be up- or down-regulated upon cold acclimation. DNA inserts of seven clones, ranging in size from 200 to 500 bp, were sequenced and the resulting sequences were compared with the NCBI non-redundant sequence database and three clones were left with unknown functions. The seven clones and the found homology of four of them are shown in Table 1 below.

TABLE 1

List of selected cold induced cDNAs

| Clone identity | Insert size (bp) | Sequence homology | Accession number |
|---|---|---|---|
| DACOR-1.3 | 316 | *Brassica napus* Galactinol synthase | CA748463 |
| DACOR-0.7 | 614 | *Oryza sativa* Glutaredoxin | AF374461 |
| DACOR-1.0 | 831 | *Arabidopsis thaliana* UBQ 15/UBQ7 | AY090541 |
| DACOR-2.0 | 1730 | *A. thaliana* Piruvate kinase-like protein | AY090539 |
| DACOR-0.9 | 184 | Unknown | CA748460 |
| DACOR-0.8 | 191 | Unknown | CA748461 |
| DACOR-0.65 | 346 | Unknown | CA748462 |

EXAMPLE 3

Sequence Analysis and Characterization of Cold Acclimation Responsive Gene DaRub1

A 260-bp differential clone, D0-B1, was isolated from total RNA from cold-acclimated *Deschampsia antarctica* plants and unveiled a ca. 1.0 kb transcript in Northern blots. In order to isolate the full-length cDNA, a cDNA library ($95 \times 10^4$ pfu), prepared from total RNA isolated from cold-acclimated *Deschampsia antarctica* leaves, was screened with the 260 bp insert as the probe. An 831 bp cDNA, DACOR-1.0 was isolated. This cDNA has a putative open reading frame (ORF) of 462 bp, flanked by a 120 bp 5' untranslated region and a 3' UTR of 249 bp that includes a 28 bp poly-A tail. FIG. 1 shows the full length sequence (SEQ ID NO: 1) of the gene. Database searches revealed that the putative ORF encodes a polypeptide of 153 amino acids (SEQ ID NO: 4) that consists of an ubiquitin monomer fused in frame to an ubiquitin-like protein RUB (related to ubiquitin). BLAST analysis showed that the RUB moiety is almost identical to other plant members of the RUB family of proteins. Two of the three *Arabidopsis* RUB genes, AtRUB1 and AtRUB2, are also fusions of the RUB coding region with that of ubiquitin. Like ubiquitin, RUB proteins are 76 amino acids in length, but share only 52-63% sequence identity with ubiquitin (FIG. 1B).

EXAMPLE 4

Regulation of Transcript Levels by Cold Acclimation

Figure 2:
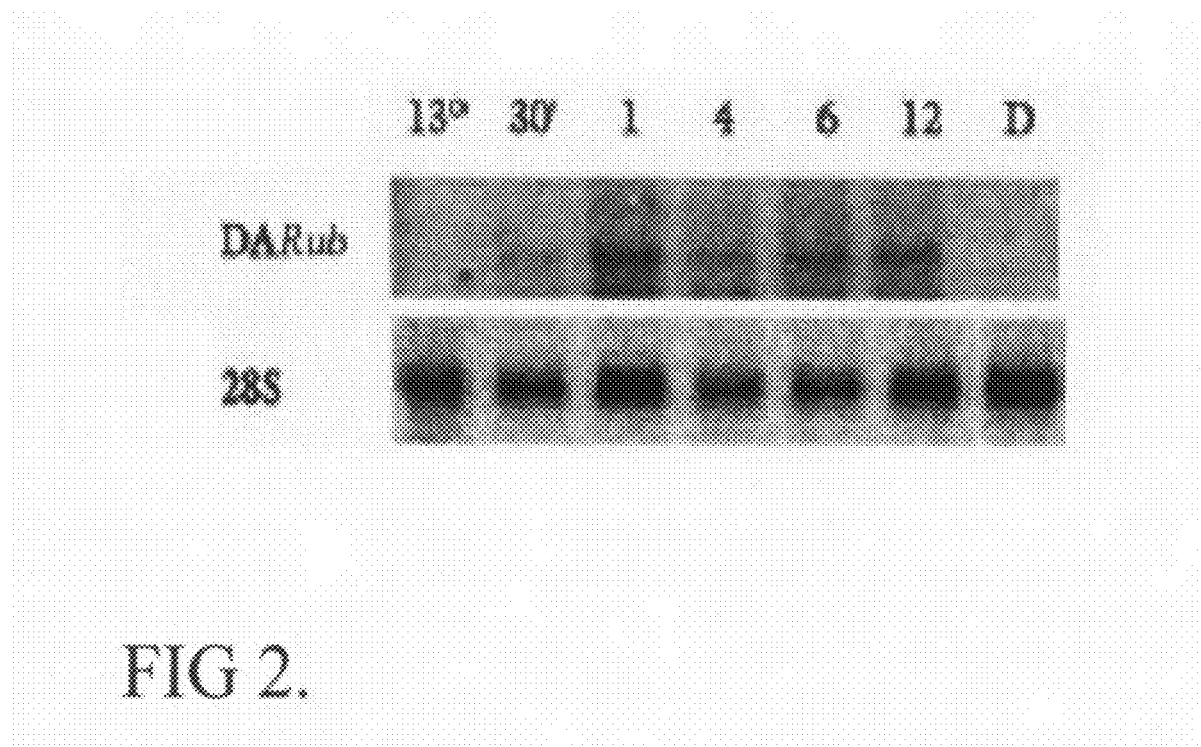
FIG. 2. Northern blot analysis of DaRub1 transcript levels in leaves of *Deschampsia antarctica* cold acclimated plants at different times: 30 mm, 1, 4, 6 and 12 hours. Control plants were kept at 13° C. Deacclimated plants were 24 h at 14° C. Total RNA (10ug) was separated on formaldehyde/1% agarose gels and probed with the 3'UTR region of the corresponding cDNA clones. A 28S ribosomal RNA probe was used as loading control on the same membranes. The plant material used for each gel is identified on the upper-most line as follows: 13° depicts the control plants kept at 13° C., 30' depicts plants cold acclimated for 30 minutes, 1 depicts plants acclimated for one hour. 4 depicts plants acclimated for four hours, 6 depicts plants acclimated for six hours, 12 depicts plants acclimated for 12 hours and D depicts plants deacclimated for 24 hours at 14° C.
Figure 3:
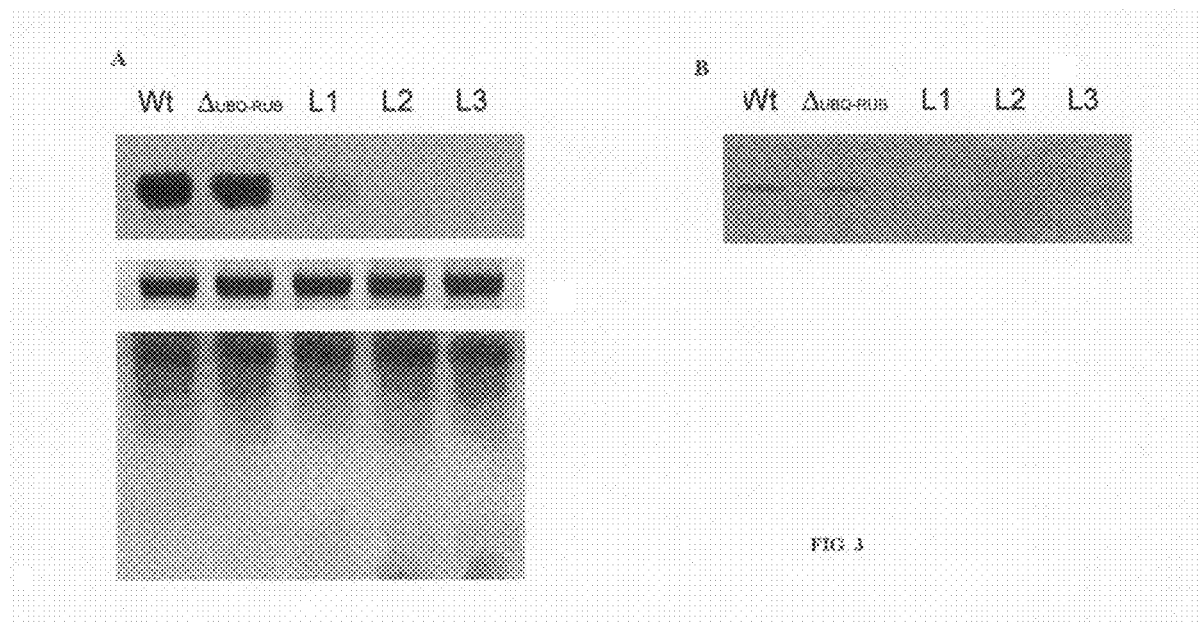
FIG. 3. A and B. To test silencing of the UBQ-RUB gene Northern and Western analysis were performed using three different transgenic lines (L1, L2, and L3) and the wild type. As a negative test transgenic line ΔAUBO-RUB was used. In this line the vector used for transformation did not contain the UBO-RUB gene. Briefly, total RNA was isolated with TRIZOL (Promega). dsRNA was obtained by digesting total RNA with RNAse I (Promega) (0.5 Units/μg of total RNA) at 37° C. for 3 hours. For Northern blot analysis, total RNA was fractionated on 1.2% formaldehyde-agarose gels, transferred to Hybond membranes and hybridized with $^{32}$P-labeled UBQ-RUB probes. siRNA analysis was performed according to Liave et al. The probe for UbiRub siRNA analysis was obtained by T7 RNA polymerase in vitro-transcription using $^{32}$P-UTP and corresponded to the 350 nt UBQ-RUB 3'-UTR. For western analysis, plant tissue was homogenized in buffer Laemimli (5% glycerol, 1% SDS, 2.5% β-mercaptoetanol, Tris-HCl 60 mM pH 6.8). Total protein extracts (15 μg) were separated by SDS-PAGE and electro-transferred to nitrocellulose membranes. An anti-UBQ-RUB polyclonal antibody was used (1:2500 dilution). The signal was visualized with an anti-rabbit antibody conjugated to phosphatase alkaline.

To investigate the regulation of DaRub1 during cold acclimation, total RNA was extracted from leaves of *Deschampsia antarctica* at various time points of cold acclimation treatment. There was no detectable signal for the gene in total RNA samples from young leaves, although rather low signal was found in older leaves. Due to the presence of the ubiquitin encoding moiety of the gene DaRub1, which in other systems seems to be encoded by a family of genes, the Northern blots were probed with the 3'UTR of the cDNA clone DACOR-1.0. Cold-acclimated leaves accumulated mRNA of DaRub1 as early as 30 min (FIG. 2). Northern blots at other time points of the 21 days cold acclimation treatment indicated that DaRub 1 was up regulated during cold acclimation and messages were found throughout the cold treatment. The transcripts declined rapidly to control levels 24 hours after the plants were returned to 13° C.

EXAMPLE 5

Isolation and Analysis of the DaRub1 Promoter

For promoter isolation, genomic DNA was isolated through a CsCl gradient. For DaRub1 primer extension analysis, total RNA was extracted from cold-acclimated plants (30 min to 24 hours) using Concert™ Plant RNA Reagent (Invitrogen) following the instructions of the manufacturer. Quality of total RNA was checked by electrophoresis on 1× TAE agarose gels. Primer extension analysis was performed using the 5'-TCTTCTCCTCCTGCTCCCGT-GTGGC-3' (SEQ ID NO:5) primer.

GenomeWalker libraries were prepared from *D. antarctica* genomic DNA using the Universal GenomeWalker™ kit (Clontech, Palo Alto, Calif., USA) following the instructions of the manufacturer. Three gene specific primers (GSP) were designed from DaRub1 cDNA sequence:

```
GSP1:
                                        (SEQ ID NO: 6)
5'-GGGTCAAGGAGAGAGCGTCAAGTCTG-3'

GSP2:
                                        (SEQ ID NO:7)
5'-AAGTCTGCGTGAGAACGAAGCGGAGGC-3';
and GSP3:
                                        (SEQ ID NO: 8)
5'-GAACGAAGCGGAGGCAGAAACAAACG-3'
```

In order to confirm the co-linearity of the putative promoter fragment and the previously isolated DaRub1 cDNA the following two primers were designed:

```
Pro-F:
                                        (SEQ ID NO: 9)
5'-CGTCTCAGTCCCCGTTGC-3';
and Pro-R:
                                       9SEQ ID NO: 10)
5'-TCGCTGCTCTCCACCTCG-3'.
```

Resulting promoter fragments were cloned into pGEM T-Easy vector (Promega, Madison, Wis., USA).

Sequencing of the amplified fragments was performed in an automatic sequencer using ABI PRISM Big Dye Terminator Cycle Sequencing Ready Reaction Kit (PROMEGA, Southampton, UK). The obtained sequences were analyzed for regulatory sequences and promoter-like elements using the MathInspector program.

From the third PCR reaction two fragments were isolated; one being 1200 pb and originating from the third GWB (DL3: PvuI) and another of 566 pb originating from the fourth GWB (DL4: StuI). Both PCR fragments (1200 pb and 566 pb) were cloned in pGEM T Easy vector (Promega) and their adequate insertion in the vector MCS was analyzed.

The cloned fragments were sequenced and their sequences analyzed. DL4 GWB fragments have high similarity with 3'-terminal sequence of the DL3 GWB. DL3 GWB (1200 pB) fragment sequence was analyzed with the MathInspector program for regulatory sequences and promoter-like elements. Several typical eukaryotic and plant regulatory sequences were found but only those directly related to DaRub1 gene characteristic or function were taken into account. The most important elements found were the Ethylene Response Element (ERE), Auxin Response Element (AuxRE) and Dehydration Response Element (DRE) (FIG. 4)

Two primers were designed to amplify a 672 bp fragment spanning the promoter 3'-terminal sequence and cDNA 5'-terminal sequence. This 672 bp fragment was used to determine the transcription star site (TSS) and to verify promoter sequence (GW product) and cDNA sequence co-linearity. TSS was determined by the primer extension method. TSS resulted to be a G, which was found 50 bp downstream of the putative TATA box. FIG. 4 shows the putative promoter sequence (SEQ ID NO: 2) and the responding elements obtained with the MathInspector Program, as well as the putative TATA box.

EXAMPLE 6

Construction of Promoter-GUS fusion and study of DaRub1 Putative Functionally

To study the putative promoter functionality, different reporter fusions were carried out with the promoter and its deletions (FIG. 5). For reporter fusion construction, the putative promoter and its deletions were fused to the gusA reporter gene in the "Promoterless" pCAMBIA 1391 vector (CAMBIA, Camberra, Australia). Each one of the promoter or deletions -pCAMBIA1391 fusions was analyzed by restriction and/or Southern blot analysis. Once verified, each fusion was introduced into *Agrobacterium tumefaciens* by electroporation. Adequate introduction was verified by Southern blot analysis.

All fusions were introduced into *Arabidobsis thaliana* Columbia by the Floral Dip method. pCAMBIA1303 vector having the 5'GusA-mgfp5*-3' fusion under the control of the 35S CaMV promoter was used as a transformation control (FIG. 6). For the selection of putative transgenic plants, seeds from T0 plants were germinated in MS medium supplemented with 25 mg/l hygromycin. Survival plantlets were removed and transplanted to the soil and the cycle was repeated until T3 plants generation.

Transgenic plants obtained for each one of the fusions (FIG. 5) were studied for cold acclimation, de-acclimation and other related stress by random selection of several plantlets. Only those transgenic lines originating from the complete promoter region fusion were capable of inducing GUS expression (FIG. 6). Results prove that this promoter region needs all its regulatory elements to induce gene expression.

Analysis was carried out in different organs of mature transgenic plants, such as flowers, siliques leaves, senescent leaves and roots. We also analyzed GUS expression in whole in vitro plantlets. Mature plants were also analyzed after wounding (detachment of leaf or aphis infection).

FIG. 6 shows that during cold acclimation at 4° C., GUS expression was observed in roots as well as in apex, fundamentally in the zones with greater meristematic tissue. This result is in agreement with Northern blots as in FIG. 2, which shows accumulation of DaRub1 mRNA as early as 30 minutes of acclimation. The expression was the highest during the first hour of acclimation, maintained during the second hour and subsequently with a similar intensity at 6 and 12 hours.

We studied expression in relation to different auxin (2,4-D) concentrations as well. Auxin treatment was carried out by transferring plants for 18 hours to liquid MS medium supplemented with 10 nM, 1.0 uM and 10 mM of 2,4-D. GUS expression induced by auxin was a little more intense than GUS expression induced by cold but less than GUS expression induced by 35S promoter region in pCAMBIA 1303 (FIG. 6). This expression was maintained in the main cellular growth and development zone, meristematic tissue, apex and root growth zone. No remarkable differences were detected with different auxin concentrations used ((10 nM, 1.0 uM, and 10 uM). This is a surprising result, because the DaRub1 promoter has to AuxRE-regions (FIG. 4).

FIG. 9 shows the model according to this disclosure which explains the importance of the two AuxRE-regions present in the DaRub1 promoter. The AuxinRE-regions (TGTC(T)C) identified in the DaRub1 promoter region are recognized by the Auxin Response Transcription Factors (ARFs: auxin response factors). Synthetic palindromic or direct repeats of these six nucleotides are sufficient to bind ARFs and confer auxin regulation on the transcription of the reporter gene. In the promoter deletions where either of the AuxER was lacking (FIG. 5) GUS expression was not induced because both of the regions are required for folding of the promoter region so that ARFs can be recognized as shown in FIG. 9. Thus, ARF mediates auxin-regulated gene expression through binding to AuxER, and AUX/IAA has the potential to alter the transcription of auxin-inducible genes by interaction with ARFs.

No synergistic effect in GUS expression was observed when plantlets were cold acclimated and auxin treated simultaneously When mature plants (approximately 2-3 weeks in greenhouse) were cold acclimated, GUS expression was as in in vitro plantlets. Interestingly, a clear GUS expression was observed in senescent leaves (FIG. 7C). This expression is probably related to the ERE present in the promoter region.

We studied GUS expression in relation to other stress factors and could only find expression related to wounding. As seen in FIG. 7A and B expression was located around the wounds. In FIG. 7A it can be seen that GUS expression is found only around the injury caused by detachment of the leaf and on both sides of the wound. This expression was seen just some minutes after the wounding. In FIG. 7B the wound is caused by an insect (aphis) and GUS expression was detected for a much longer period than the expression induced by leaf detachment.

In FIGS. 7D-H, it can be seen that GUS expression changes during different flower development phases: expression is strong in early flower development phase and less intense in advanced stages. FIGS. 7 D, E, F and G show expression in pollen. FIG. 7 H shows an advanced phase after floral anthesis and GUS expression is observed only in the growth and elongation zones of the meristematic tissue in the flower base. In FIG. 7I it can be seen that once the siliques are formed GUS expression is limited to the seed funicular.

EXAMPLE 7

Study of DaRub1 Expression in *D. antarctica* by in situ Hybridization

A 190 bp fragment, which included the 3'UTR, was amplified using DaRub1 cDNA and the primers 5'-CCTGT-GTGTAACATCAGACTCTCTCCAC-3' (SEQ ID NO: 11) and 5'TCCACTTCTGCCCAATGCTAACTCC-3' (SEQ ID NO: 12.) The amplified product was cloned in pGEM® T-Easy vector (Promega). Labeling was carried out by the Digoxigenin RNA labeling kit (Roche), following manufacturer's instructions. Sense and antisense probes were used.

*D. antarctica* plants were acclimated at 4° C. for 24 hours. Hybridization was performed according to Jackson (1991) with some modifications (Vielle Woen et al, 1999). 400 to 800 ng of RNA probes were utilized for each reaction. Hybridization was carried out at 55° C. overnight. Specific hybridization signals were detected by incubating the hybridized slides in labeled antidigoxigenin antibodies according to standard protocols. Analysis was carried out with a microscope Leica DMRB under brilliant field and optical Nomarski. In situ hybridization with the antisense RNA probe (FIG. 8) showed gene expression in meristematic tissues in good agreement with GUS expression controlled by DARub1 promoter in *A. thaliana*. This result suggests that the isolated promoter region contains all the necessary controlling elements to regulate DARub1 expression

EXAMPLE 8

Plant Transformation Process with *Eucalyptus globulus*

Genetic transformation of *Eucalyptus globulus* elite individuals via *Agrobacterium tumefaciens* was carried out according to the procedure described for recalcitrant species by Perez—Molphe & Ochoa-Alejo N. (1998) with some modifications. *Agrobacterium tumefaciens* hypervirulent strain AGLθ was used. A single *Agrobacterium* colony was inoculated into 25 ml of YEP media (yeast extract 20 g., peptone 20 g, NaCl 10 g.) together with the selection antibiotics, hygromycin 100 mg/L, rifampicin 100 mg/L, and cloramphenicol 250 mg/L. The culture was incubated at 28° C. and at 150 rpm until it reached an $OD_{600}$ of 0.5. The culture was then centrifuged a 3000×g for 20 min, resuspended in diluted MS media 1:10 and supplemented with 50 μl of acetosyringone. Before use the suspension was incubated for 5 hours at 28° C. and at 100 rpm.

The tissue was prepared for transformation by selecting shoots that corresponded to the second and third internodes of the in vitro cultivated plants. Additionally, longitudinal wounds were performed at both sides of the stem after which the explants were transferred to an Erlenmeyer containing the *Agrobacterium* suspension.

The explants were incubated in the *Agrobacterium* suspension for 10 min under vacuum. Thereafter they were dried with sterile filter paper and transferred to the cocultivation media (MS [½] without hormones) placing them horizontally for 2 days. After this, the explants were rinsed in liquid MS plus cefotaxime 250 mg/mL to prevent *Agrobacterium* overgrowth, dried with sterile filter paper and placed vertically on selection media (MS, sucrose 3%, BAP 0.1 mg/mL, NAA 0.01 mg/mL, cefotaxime 250 mg/mL, kanamycin 100 mg/mL or hygromycin 15 mg/mL). The explants were transferred to fresh new media every 7 days for the first 4 weeks.

Putative transgenic explants were transferred to rooting media (MS [½], IBA 2 mg/L, sucrose 20 g/L, agar 8 g/L, pH 5.8 with selection antibiotics) where roots developed after 2 weeks.

Five transgenic Eucalyptus lines all of which expressed DaRub1 gene were regenerated.

EXAMPLE 9

Physiological and Biochemical Characterization of DaRub1 Transgenic *Eucalyptus* Plants Lethal Temperatures for 50% of Leaf Tissue ($TL_{50}$) were analyzed for five transgenic *Eucalyptus* lines and two wild type lines according to the methodology of Cloutier and Andrews (1984), with slight modifications (Alberdi et al., 1993). The leaves were placed in tight glass containers, AgI and $H_2O$ were added to prevent supercooling and to secure freezing of the samples. The glass containers were placed in a cryostat and exposed to freezing temperatures (approx. between −1 and −30° C.) for 120 minutes. After that the samples were thawed at 4° C. for many hours. Deionized water was added to the samples, stirred at 29° C. for 1 hour, and ion leakage was measured by conductivity. $TL_{50}$ corresponds to the temperature at which 50% of the dead tissue conductivity in liquid nitrogen is reached. This analysis was carried out first with control plants (wild type lines), and according to the results the conditions for cold acclimation and freezing were determined and used for the evaluation of the transgenic plants.

Table 2 below shows the freezing temperatures (upper and lower limits) of transgenic lines 1-5 and two wild type lines. The table also shows ice nucleation temperatures of the plants. The lines have been ranked based on the freezing tolerance as deduced from the Lt50 value and the ice nucleation temperature. It can be clearly seen that all of the transgenic lines were more tolerant to freezing stress than the control lines and that lines 3 and 5 show the best freezing tolerance.

TABLE 2

| | | Nucleation temperature ° C. | | Freezing temperature ° C. | |
|---|---|---|---|---|---|
| Line | Ranking | Lower limit | Upper limit | Lower limit | Upper limit |
| 5 transgenic | 1 | −8.83 | −7.77 | −5.73 | −5.08 |
| 3 transgenic | 2 | −8.32 | 7.43 | −4.70 | −4.36 |
| 2 transgenic | 3 | −7.61 | −7.2 | −5.22 | −4.50 |

TABLE 2-continued

|  |  | Nucleation temperature ° C. | | Freezing temperature ° C. | |
| --- | --- | --- | --- | --- | --- |
| Line | Ranking | Lower limit | Upper limit | Lower limit | Upper limit |
| 1 transgenic | 4 | −7.25 | −6.73 | −5.24 | −4.19 |
| 4 transgenic | 5 | −7.4 | −6.66 | −4.55 | −3.86 |
| 6 wild type | 6 | −5.03 | −4.43 | −3.50 | −2.84 |
| 7 wild type | 7 | −5.31 | −3.97 | −3.66 | −2.40 |

Transgenic and wild type plants were also evaluated based on the physiological state of photosystem II (PSII) at low temperatures during cold acclimation and freezing by monitoring PSII fluorescence in the leaves. Fluorescence was measured with a pulse amplitude fluorimeter (Hansatech). Table 3 below shows the order of average percentage of photo inhibition of the leaves at different freezing temperatures. Clearly, transgenic lines (1 to 5) possessed less photo inhibition at low temperatures, thereby showing better low temperature tolerance compared to the wild type lines (lines 6 and 7). Again transgenic lines 3 and 5 showed the best low temperature tolerance of all transgenic lines.

TABLE 3

| Temperature ° C. | | | | |
| --- | --- | --- | --- | --- |
| −3 | −5 | −7 | −9 | −11 |
| 5 | 3 | 3 | 5 | 5 |
| 3 | 5 | 5 | 3 | 3 |
| 2 | 2 | 4 | 4 | 2 |
| 4 | 1 | 4 | 4 | 4 |
| 1 | 1 | 4 | 1 | 4 |
| 7 | 7 | 6 | 6 | 6 |
| 6 | 6 | 7 | 7 | 7 |

The freezing damage of transgenic and wild type *Eucalyptus* leaves were also evaluated visually. Freezing damage in *Eucalyptus* leaves can be detected by color change in the central vein which turns red. This experiment also showed that transgenic lines were clearly more freezing tolerant than wild type plants: central veins of wild type plants turned reddish at −3° C. and red at −5° C.; while the leaves of all transgenic lines showed reddish central veins at temperatures lower than for wild type plants.

What is claimed is:

1. An isolated plant promoter comprising a nucleotide sequence of SEQ ID NO: 2.

2. The promoter according to claim 1, wherein the promoter is inducible by a low temperature of 4° C.

3. The promoter according to claim 1, wherein the promoter is inducible by wounding.

4. The promoter according to claim 1, wherein the promoter is inducible by auxin.

5. An expression cassette comprising a promoter of SEQ ID NO: 2 said promoter being operably linked to a nucleic acid sequence encoding a desired polnucleotide of interset.

6. A plant cell comprising the expression cassette of claim 5.

7. A transgenic plant, comprising the expression cassette of claim 5.

8. The plant of claim 7, wherein said plant is a dicotyledon.

9. A method to inducibly express a desired polynucleotide of interest in a plant, said method comprising the steps of: a) transforming a plant cell with the expression cassette of claim 5; b) regenerating a whole plant from the cell; and c) expressing the desired polynucleotide of interest by subjecting the plant to inductive conditions.

10. The method of claim 9, wherein the inductive condition is a low temperature of 4° C.

11. The method of claim 9, wherein the inductive condition is wounding of the plant tissue.

12. The method of claim 9, wherein the inductive condition is providing auxin to the plant tissue.

13. The method of claim 9, wherein the plant is a dicotyledon.

* * * * *

SEQUENCE LISTING

```
<160> NUMBER OF SEQ ID NOS: 13

<210> SEQ ID NO 1
<211> LENGTH: 1920
<212> TYPE: DNA
<213> ORGANISM: Deschampsia antarctica
<220> FEATURE:
<221> NAME/KEY: promoter
<222> LOCATION: (1)..(1089)
<220> FEATURE:
<221> NAME/KEY: 5'UTR
<222> LOCATION: (1089)..(1209)
<220> FEATURE:
<221> NAME/KEY: misc_feature
<222> LOCATION: (1209)..(1920)
<223> OTHER INFORMATION: coding sequence plus poly-A tail

<400> SEQUENCE: 1
ctgtttggct ttatttataa agcggaacga aagcctgttt cgaaaagaga gaagtcacga      60
cggaccaaac ccatttagag tagcgacact cgatgcctcg ccattttcgt gaggaatttc     120
catagttggc aagtgatgtc acctacttca tggtgcattt agagttgagg cagagcttac     180
ccggcatgtg taagggtggc aatattcact gtggggacga gtaccgcgg ggagttaccc      240 atcatgaagc ggagatgggg gacaaattca ccccacgggt attgtctcat ggggcgggga     300
tggggagcaa atcctccatg gatacccgac gaactatgcc atgtgaacta cagatgcaca     360
```

-continued

```
atatatagat taaaacctag atagtccact taattttttt tctccatctc tctcagccac    420
cttgtccttt ctaatctcat ttatcacagt cgacgctgag ttcccataga gtcccgacgg    480
gtaccggata cccgttattg acagggatgg ggacagtttt gtccccgtga aggtttatgg    540
ggctggcggg tatgaggact ggtggggttc gaggtgagga cggcggagtc atcaccggtc    600
gtctcagtcc ccgttgccac cctgaggcgt gagcagaact taggtcgctc ttgccaatat    660
aggtcaaacg gaagctagaa ctgatgcgtg gcttcgttca gggccagcaa acatacctca    720
actctgtttc gaggattgta atccggttgc tttaagtccc ataccacccc attcgcgaaa    780
aggaaaaacg aaaaggatt ttgagtagac gagtttttac atgcgacgca agccgatggg    840
tgtccaaacc agttcgtctg tacgtccgtg gcatttcgtg tgcacaacag cacgagtata    900
acattttata cgtacctgaa gattaggatc aagcgtcttg catagtctca ggagaaggaa    960
aaaaaaaagg tcccaaccga cgttacagaa cgggtcggaa gtctgagccc gagcggaaaa   1020
ccggctcacg gggttccccc gacttgacgc gcgcacccct caataaatcc accgggtccc   1080
gaggaaaaag aaaggaattt tcgtttgttt ctgcctccgc ttcgttctca cgcagacttg   1140
acgctctctc cttgaccccc ctccctccac cctccaggcc tcgccgccac acgggagcag   1200
gaggagaaga tgcagatctt cgtcaagacc ctgacgggga agaccatcac cctcgaggtg   1260
gagagcagcg acaccatcga taacgtcaag gccaaaatcc aggacaaaga agggattcct   1320
ccagaccaac aacgtttgat atttgctggc aagcagttgg aagatggacg cacacttgct   1380
gattacaata ttcaaaagga gtctactctt cacttggtcc tcaggctcag gggcggtact   1440
atgatcaagg ttaagacact cactggaaag gagatcgaaa ttgacattga gcccactgac   1500
acgattgata gggtcaagga gcgtgttgag gagaaagaag gcattcctcc cgtgcagcaa   1560
aggttgattt atgctggtaa gcagcttgca gatgacaaga ctgcgaagga ctacaacatc   1620
gaaggtggct ccgtcctcca tcttgtactt gctctgaggg gtggttacta gtaaatctag   1680
ctagtgacac tacttgcctc aatctactct aatggttgag agaagtgact attggtggta   1740
tggaactaga taataacaag taacaaacta gcttttccta gtgggagggg ctgtcttcca   1800
tgttattatc ttgtatgatt tgataaaatc actcccagt ttatctgcct ctgttgttat   1860
gtctgctgtg tgagaaaatc catgatcatc tgaaaaaaa aaaaaaaaa aaaaaaaaa    1920
```

<210> SEQ ID NO 2
<211> LENGTH: 1089
<212> TYPE: DNA
<213> ORGANISM: Deschampsia antractica
<220> FEATURE:
<221> NAME/KEY: promoter
<222> LOCATION: (1)..(1089)

<400> SEQUENCE: 2

```
ctgtttggct ttatttataa agcggaacga aagcctgttt cgaaaagaga gaagtcacga     60
cggaccaaac ccatttagag tagcgacact cgatgcctcg ccattttcgt gaggaatttc    120
catagttggc aagtgatgtc acctacttca tggtgcattt agagttgagg cagagcttac    180
ccggcatgtg taagggtggc aatattcact gtggggacga gtacccgcgg ggagttaccc    240
atcatgaagc ggagatgggg gacaaattca ccccacgggt attgtctcat ggggcgggga    300
tggggagcaa atcctccatg gatacccgac gaactatgcc atgtgaacta cagatgcaca    360
atatatagat taaaacctag atagtccact taattttttt tctccatctc tctcagccac    420
cttgtccttt ctaatctcat ttatcacagt cgacgctgag ttcccataga gtcccgacgg    480
```

```
gtaccggata cccgttattg acagggatgg ggacagtttt gtccccgtga aggtttatgg      540
ggctggcggg tatgaggact ggtggggttc gaggtgagga cggcggagtc atcaccggtc      600
gtctcagtcc ccgttgccac cctgaggcgt gagcagaact taggtcgctc ttgccaatat      660
aggtcaaacg gaagctagaa ctgatgcgtg gcttcgttca gggccagcaa acatacctca      720
actctgtttc gaggattgta atccggttgc tttaagtccc ataccacccc attcgcgaaa      780
aggaaaaacg aaaaggatt ttgagtagac gagttttttac atgcgacgca agccgatggg      840
tgtccaaacc agttcgtctg tacgtccgtg gcatttcgtg tgcacaacag cacgagtata      900
acattttata cgtacctgaa gattaggatc aagcgtcttg catagtctca ggagaaggaa      960
aaaaaaaagg tcccaaccga cgttacagaa cgggtcggaa gtctgagccc gagcggaaaa     1020
ccggctcacg gggttccccc gacttgacgc cgcgcaccct caataaatcc accgggtccc     1080
gaggaaaaa                                                             1089

<210> SEQ ID NO 3
<211> LENGTH: 459
<212> TYPE: DNA
<213> ORGANISM: Deschampsia antarctica
<220> FEATURE:
<221> NAME/KEY: CDS
<222> LOCATION: (1)..(459)

<400> SEQUENCE: 3 atg cag atc ttc gtc aag acc ctg acg ggg aag acc atc acc ctc gag       48
Met Gln Ile Phe Val Lys Thr Leu Thr Gly Lys Thr Ile Thr Leu Glu
1               5                   10                  15 gtg gag agc agc gac acc atc gat aac gtc aag gcc aaa atc cag gac       96
Val Glu Ser Ser Asp Thr Ile Asp Asn Val Lys Ala Lys Ile Gln Asp
            20                  25                  30 aaa gaa ggg att cct cca gac caa caa cgt ttg ata ttt gct ggc aag      144
Lys Glu Gly Ile Pro Pro Asp Gln Gln Arg Leu Ile Phe Ala Gly Lys
        35                  40                  45 cag ttg gaa gat gga cgc aca ctt gct gat tac aat att caa aag gag      192
Gln Leu Glu Asp Gly Arg Thr Leu Ala Asp Tyr Asn Ile Gln Lys Glu
    50                  55                  60 tct act ctt cac ttg gtc ctc agg ctc agg ggc ggt act atg atc aag      240
Ser Thr Leu His Leu Val Leu Arg Leu Arg Gly Gly Thr Met Ile Lys
65                  70                  75                  80 gtt aag aca ctc act gga aag gag atc gaa att gac att gag ccc act      288
Val Lys Thr Leu Thr Gly Lys Glu Ile Glu Ile Asp Ile Glu Pro Thr
                85                  90                  95 gac acg att gat agg gtc aag gag cgt gtt gag gag aaa gaa ggc att      336
Asp Thr Ile Asp Arg Val Lys Glu Arg Val Glu Glu Lys Glu Gly Ile
            100                 105                 110 cct ccc gtg cag caa agg ttg att tat gct ggt aag cag ctt gca gat      384
Pro Pro Val Gln Gln Arg Leu Ile Tyr Ala Gly Lys Gln Leu Ala Asp
        115                 120                 125 gac aag act gcg aag gac tac aac atc gaa ggt ggc tcc gtc ctc cat      432
Asp Lys Thr Ala Lys Asp Tyr Asn Ile Glu Gly Gly Ser Val Leu His
    130                 135                 140 ctt gta ctt gct ctg agg ggt ggt tac                                   459
Leu Val Leu Ala Leu Arg Gly Gly Tyr
145                 150

<210> SEQ ID NO 4
<211> LENGTH: 153
<212> TYPE: PRT
<213> ORGANISM: Deschampsia antarctica
```

<400> SEQUENCE: 4

```
Met Gln Ile Phe Val Lys Thr Leu Thr Gly Lys Thr Ile Thr Leu Glu
1               5                   10                  15
Val Glu Ser Ser Asp Thr Ile Asp Asn Val Lys Ala Lys Ile Gln Asp
            20                  25                  30
Lys Glu Gly Ile Pro Pro Asp Gln Gln Arg Leu Ile Phe Ala Gly Lys
        35                  40                  45
Gln Leu Glu Asp Gly Arg Thr Leu Ala Asp Tyr Asn Ile Gln Lys Glu
    50                  55                  60
Ser Thr Leu His Leu Val Leu Arg Leu Arg Gly Gly Thr Met Ile Lys
65                  70                  75                  80
Val Lys Thr Leu Thr Gly Lys Glu Ile Glu Ile Asp Ile Glu Pro Thr
                85                  90                  95
Asp Thr Ile Asp Arg Val Lys Glu Arg Val Glu Glu Lys Glu Gly Ile
            100                 105                 110
Pro Pro Val Gln Gln Arg Leu Ile Tyr Ala Gly Lys Gln Leu Ala Asp
        115                 120                 125
Asp Lys Thr Ala Lys Asp Tyr Asn Ile Glu Gly Gly Ser Val Leu His
    130                 135                 140
Leu Val Leu Ala Leu Arg Gly Gly Tyr
145                 150
```

<210> SEQ ID NO 5
<211> LENGTH: 153
<212> TYPE: PRT
<213> ORGANISM: Deschampsia antarctica

<400> SEQUENCE: 5

```
Met Gln Ile Phe Val Lys Thr Leu Thr Gly Lys Thr Ile Thr Leu Glu
1               5                   10                  15
Val Glu Ser Ser Asp Thr Ile Asp Asn Val Lys Ala Lys Ile Gln Asp
            20                  25                  30
Lys Glu Gly Ile Pro Pro Asp Gln Gln Arg Leu Ile Phe Ala Gly Lys
        35                  40                  45
Gln Leu Glu Asp Gly Arg Thr Leu Ala Asp Tyr Asn Ile Gln Lys Glu
    50                  55                  60
Ser Thr Leu His Leu Val Leu Arg Leu Arg Gly Gly Thr Met Ile Lys
65                  70                  75                  80
Val Lys Thr Leu Thr Gly Lys Glu Ile Glu Ile Asp Ile Glu Pro Thr
                85                  90                  95
Asp Thr Ile Asp Arg Val Lys Glu Arg Val Glu Glu Lys Glu Gly Ile
            100                 105                 110
Pro Pro Val Gln Gln Arg Leu Ile Tyr Ala Gly Lys Gln Leu Ala Asp
        115                 120                 125
Asp Lys Thr Ala Lys Asp Tyr Asn Ile Glu Gly Gly Ser Val Leu His
    130                 135                 140
Leu Val Leu Ala Leu Arg Gly Gly Tyr
145                 150
```

<210> SEQ ID NO 6
<211> LENGTH: 25
<212> TYPE: DNA
<213> ORGANISM: Deschampsia antarctica
<220> FEATURE:
<221> NAME/KEY: misc_feature
<222> LOCATION: (1)..(25)
<223> OTHER INFORMATION: primer -continued

```
<400> SEQUENCE: 6
tcttctcctc ctgctcccgt gtggc                                          25

<210> SEQ ID NO 7
<211> LENGTH: 26
<212> TYPE: DNA
<213> ORGANISM: Deschampsia antarctica
<220> FEATURE:
<221> NAME/KEY: misc_feature
<222> LOCATION: (1)..(26)
<223> OTHER INFORMATION: primer

<400> SEQUENCE: 7
ggtcaaggag agaggcgtca agtctg                                         26

<210> SEQ ID NO 8
<211> LENGTH: 26
<212> TYPE: DNA
<213> ORGANISM: Deschampsia antarctica
<220> FEATURE:
<221> NAME/KEY: misc_feature
<222> LOCATION: (1)..(26)
<223> OTHER INFORMATION: primer

<400> SEQUENCE: 8
aagtctgcgt gagaacgaag cggagc                                         26

<210> SEQ ID NO 9
<211> LENGTH: 26
<212> TYPE: DNA
<213> ORGANISM: Deschampsia antarctica
<220> FEATURE:
<221> NAME/KEY: misc_feature
<222> LOCATION: (1)..(26)
<223> OTHER INFORMATION: primer

<400> SEQUENCE: 9
gaacgaagcg gaggcagaaa caaacg                                         26

<210> SEQ ID NO 10
<211> LENGTH: 16
<212> TYPE: DNA
<213> ORGANISM: Deschampsia antarctica
<220> FEATURE:
<221> NAME/KEY: misc_feature
<222> LOCATION: (1)..(16)
<223> OTHER INFORMATION: primer

<400> SEQUENCE: 10
cgtctgtccc cgttgc                                                    16

<210> SEQ ID NO 11
<211> LENGTH: 18
<212> TYPE: DNA
<213> ORGANISM: Deschampsia antarctica
<220> FEATURE:
<221> NAME/KEY: misc_feature
<222> LOCATION: (1)..(18)
<223> OTHER INFORMATION: primer

<400> SEQUENCE: 11
tcgctgctct ccacctcg                                                  18

<210> SEQ ID NO 12
<211> LENGTH: 28
<212> TYPE: DNA
```

-continued

```
<213> ORGANISM: Deschampsia antarctica
<220> FEATURE:
<221> NAME/KEY: misc_feature
<222> LOCATION: (1)..(28)
<223> OTHER INFORMATION: primer

<400> SEQUENCE: 12
cctgtgrgta acatcagact ctctccac                                          28

<210> SEQ ID NO 13
<211> LENGTH: 25
<212> TYPE: DNA
<213> ORGANISM: Deschampsia antarctica
<220> FEATURE:
<221> NAME/KEY: misc_feature
<222> LOCATION: (1)..(25)
<223> OTHER INFORMATION: primer

<400> SEQUENCE: 13
tccacttctg cccaatgcta actcc                                             25
```